(12) United States Patent
Watschke

(10) Patent No.: US 7,357,773 B2
(45) Date of Patent: Apr. 15, 2008

(54) HANDLE AND SURGICAL ARTICLE

(75) Inventor: Brian P. Watschke, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 749 days.

(21) Appl. No.: 10/739,668

(22) Filed: Dec. 18, 2003

(65) Prior Publication Data

US 2004/0133217 A1  Jul. 8, 2004

Related U.S. Application Data

(63) Continuation-in-part of application No. 10/386,897, filed on Mar. 11, 2003, now abandoned, and a continuation-in-part of application No. 10/306,179, filed on Nov. 27, 2002, now Pat. No. 7,070,556.

(60) Provisional application No. 60/362,806, filed on Mar. 7, 2002, provisional application No. 60/380,797, filed on May 14, 2002, provisional application No. 60/402,007, filed on Aug. 8, 2002, provisional application No. 60/414,865, filed on Sep. 30, 2002.

(51) Int. Cl.
*A61F 2/02* (2006.01)
(52) U.S. Cl. ........................................................ 600/29
(58) Field of Classification Search ................ D24/26, D24/27, 28, 30, 133, 145–147; 606/82–85, 606/53; 600/37, 226
See application file for complete search history.

(56) References Cited

U.S. PATENT DOCUMENTS

| | | | |
|---|---|---|---|
| 1,934,962 A * | 11/1933 | Barry | ........................... 606/84 |
| 2,738,790 A | 3/1956 | Todt et al. | |
| 3,124,136 A | 3/1964 | Usher | |
| 3,182,662 A | 5/1965 | Shirodkar | |
| 3,247,594 A * | 4/1966 | Nosonowitz | ................. 433/102 |
| 3,311,110 A | 3/1967 | Singerman et al. | |
| 3,384,073 A | 5/1968 | Van Winkle, Jr. | |
| 3,472,232 A | 10/1969 | Earl | |
| 3,580,313 A | 5/1971 | McKnight | |
| 3,763,860 A | 10/1973 | Clarke | |
| 3,789,828 A | 2/1974 | Schulte | |
| 3,858,783 A | 1/1975 | Kapitanov et al. | |
| 3,924,633 A | 12/1975 | Cook et al. | |
| 3,995,619 A | 12/1976 | Glatzer | |
| 4,019,499 A | 4/1977 | Fitzgerald | |
| 4,037,603 A | 7/1977 | Wendorff | |

(Continued)

FOREIGN PATENT DOCUMENTS

DE     2305815     2/1973

(Continued)

OTHER PUBLICATIONS

U.S. Appl. No. 09/661/620, filed Sep. 27, 2002, Suslaine et al.

(Continued)

*Primary Examiner*—Samuel G Gilbert
(74) *Attorney, Agent, or Firm*—Jose W. Jimenez; Kimberly K. Baxter; Gregory L. Koeller

(57) ABSTRACT

Handles for needles suitable for pelvic floor surgical procedures are described.

16 Claims, 7 Drawing Sheets

U.S. PATENT DOCUMENTS

| | | | |
|---|---|---|---|
| 4,128,100 A | 12/1978 | Wendorff | |
| 4,172,458 A | 10/1979 | Pereyra | |
| 4,204,541 A | 5/1980 | Kapitanov | |
| 4,235,238 A | 11/1980 | Ogiu et al. | |
| 4,246,660 A | 1/1981 | Wevers | |
| 4,265,231 A | 5/1981 | Scheller, Jr. et al. | |
| 4,441,497 A | 4/1984 | Paudler | |
| 4,509,516 A | 4/1985 | Richmond | |
| 4,632,100 A | 12/1986 | Somers et al. | |
| 4,775,380 A | 10/1988 | Seedhom et al. | |
| 4,857,041 A | 8/1989 | Annis et al. | |
| 4,865,031 A | 9/1989 | O'Keeffe | |
| 4,920,986 A | 5/1990 | Biswas | |
| 5,053,043 A | 10/1991 | Gottesman et al. | |
| 5,085,661 A | 2/1992 | Moss | |
| 5,112,344 A | 5/1992 | Petros | |
| 5,123,428 A | 6/1992 | Schwarz | |
| 5,188,636 A | 2/1993 | Fedotov | |
| 5,207,694 A | 5/1993 | Broome | |
| 5,209,756 A | 5/1993 | Seedhom et al. | |
| D338,955 S * | 8/1993 | Gresl et al. | D24/130 |
| 5,250,033 A | 10/1993 | Evans et al. | |
| 5,256,133 A | 10/1993 | Spitz | |
| 5,281,237 A | 1/1994 | Gimpelson | |
| 5,328,077 A | 7/1994 | Lou | |
| 5,336,239 A | 8/1994 | Gimpelson | |
| 5,337,736 A | 8/1994 | Reddy | |
| D350,605 S * | 9/1994 | Williams | D24/133 |
| 5,362,294 A | 11/1994 | Seitzinger | |
| 5,368,595 A | 11/1994 | Lewis | |
| 5,383,904 A | 1/1995 | Totakura et al. | |
| 5,386,836 A | 2/1995 | Biswas | |
| 5,403,328 A | 4/1995 | Shallman | |
| 5,413,598 A | 5/1995 | Moreland | |
| 5,439,467 A | 8/1995 | Benderev et al. | |
| 5,520,700 A | 5/1996 | Beyar et al. | |
| 5,520,703 A * | 5/1996 | Essig et al. | 606/148 |
| 5,544,664 A | 8/1996 | Benderev et al. | |
| 5,562,685 A | 10/1996 | Mollenauer et al. | |
| 5,562,689 A | 10/1996 | Green et al. | |
| 5,571,139 A | 11/1996 | Jenkins, Jr. | |
| 5,591,163 A | 1/1997 | Thompson | |
| D378,405 S * | 3/1997 | Musgrave et al. | D24/112 |
| 5,611,515 A | 3/1997 | Benderev et al. | |
| D379,510 S * | 5/1997 | Bays | D24/133 |
| 5,628,756 A | 5/1997 | Barker, Jr. et al. | |
| 5,633,286 A | 5/1997 | Chen | |
| 5,662,683 A | 9/1997 | Kay | |
| 5,669,935 A | 9/1997 | Rosenman et al. | |
| 5,683,349 A | 11/1997 | Makower et al. | |
| 5,807,403 A | 9/1998 | Beyar et al. | |
| 5,810,882 A | 9/1998 | Bolduc et al. | |
| 5,836,314 A | 11/1998 | Benderev et al. | |
| 5,836,315 A | 11/1998 | Benderev et al. | |
| 5,842,478 A | 12/1998 | Benderev et al. | |
| 5,860,425 A | 1/1999 | Benderev et al. | |
| 5,885,291 A * | 3/1999 | Moskovitz et al. | 606/79 |
| 5,899,909 A | 5/1999 | Claren et al. | |
| 5,904,696 A | 5/1999 | Rosenman | |
| 5,919,232 A | 7/1999 | Chaffringeon et al. | |
| 5,934,283 A | 8/1999 | Willem et al. | |
| 5,935,122 A | 8/1999 | Fourkas et al. | |
| 5,935,138 A | 8/1999 | McJames, II et al. | |
| 5,944,732 A | 8/1999 | Raulerson et al. | |
| 5,972,000 A | 10/1999 | Beyar et al. | |
| 5,988,171 A | 11/1999 | Sohn et al. | |
| 5,992,269 A | 11/1999 | Puig et al. | |
| 5,997,554 A | 12/1999 | Thompson | |
| 6,010,447 A | 1/2000 | Kardjian | |
| 6,030,393 A | 2/2000 | Corlew | |
| 6,031,148 A | 2/2000 | Hayes et al. | |
| 6,042,534 A | 3/2000 | Gellman et al. | |
| 6,042,536 A | 3/2000 | Tihon et al. | |
| 6,048,351 A | 4/2000 | Gordon et al. | |
| 6,050,937 A | 4/2000 | Benderev | |
| 6,053,935 A | 4/2000 | Brenneman et al. | |
| 6,068,591 A | 5/2000 | Bruckner et al. | |
| 6,071,290 A | 6/2000 | Compton | |
| 6,099,538 A * | 8/2000 | Moses et al. | 606/144 |
| 6,106,545 A | 8/2000 | Egan | |
| 6,110,101 A | 8/2000 | Tihon et al. | |
| 6,117,067 A | 9/2000 | Gil-Vernet | |
| 6,168,611 B1 | 1/2001 | Risvi | |
| 6,221,005 B1 | 4/2001 | Bruckner et al. | |
| 6,273,852 B1 | 8/2001 | Lehe et al. | |
| 6,302,840 B1 | 10/2001 | Benderev | |
| 6,306,079 B1 | 10/2001 | Trabucco | |
| 6,328,744 B1 | 12/2001 | Harari et al. | |
| 6,334,446 B1 | 1/2002 | Beyar | |
| 6,352,553 B1 | 3/2002 | van der Burg et al. | |
| 6,367,353 B2 | 4/2002 | Puig et al. | |
| 6,382,214 B1 | 5/2002 | Raz et al. | |
| 6,406,423 B1 | 6/2002 | Scetbon | |
| 6,406,480 B1 | 6/2002 | Beyar et al. | |
| 6,475,139 B1 | 11/2002 | Miller | |
| 6,478,727 B2 | 11/2002 | Scetbon | |
| 6,482,214 B1 | 11/2002 | Sidor, Jr. et al. | |
| 6,494,906 B1 | 12/2002 | Owens | |
| 6,502,578 B2 | 1/2003 | Raz et al. | |
| 6,530,943 B1 | 3/2003 | Hoepffner et al. | |
| 6,582,443 B2 | 6/2003 | Cabak et al. | |
| 6,626,917 B1 | 9/2003 | Craig | |
| 6,638,210 B2 | 10/2003 | Berger | |
| 6,663,633 B1 | 12/2003 | Pierson, II | |
| 6,673,010 B2 | 1/2004 | Skiba | |
| 2001/0000533 A1 | 4/2001 | Kovac | |
| 2001/0049467 A1 | 12/2001 | Lehe et al. | |
| 2002/0022841 A1 | 2/2002 | Kovac | |
| 2002/0028980 A1 | 3/2002 | Thierfelder et al. | |
| 2002/0055748 A1 | 5/2002 | Gellman et al. | |
| 2002/0058959 A1 | 5/2002 | Gellman | |
| 2002/0068948 A1 | 6/2002 | Stormby et al. | |
| 2002/0072694 A1 | 6/2002 | Snitkin et al. | |
| 2002/0077526 A1 | 6/2002 | Kammerer et al. | |
| 2002/0078964 A1 | 6/2002 | Kovac et al. | |
| 2002/0091373 A1 | 7/2002 | Berger | |
| 2002/0099258 A1 | 7/2002 | Staskin et al. | |
| 2002/0099259 A1 | 7/2002 | Anderson et al. | |
| 2002/0099260 A1 | 7/2002 | Suslaine et al. | |
| 2002/0107430 A1 | 8/2002 | Neisz et al. | |
| 2002/0107525 A1 | 8/2002 | Harari et al. | |
| 2002/0115906 A1 | 8/2002 | Miller | |
| 2002/0128670 A1 | 9/2002 | Ulmsten et al. | |
| 2002/0138025 A1 | 9/2002 | Gellman et al. | |
| 2002/0147382 A1 | 10/2002 | Neisz et al. | |
| 2002/0151762 A1 | 10/2002 | Rocheleau et al. | |
| 2002/0151909 A1 | 10/2002 | Gellman et al. | |
| 2002/0151910 A1 | 10/2002 | Gellman et al. | |
| 2002/0156487 A1 | 10/2002 | Gellman et al. | |
| 2002/0156488 A1 | 10/2002 | Gellman et al. | |
| 2002/0188169 A1 | 12/2002 | Kammerer et al. | |
| 2003/0004395 A1 | 1/2003 | Therin | |
| 2003/0009181 A1 | 1/2003 | Gellman et al. | |
| 2003/0023136 A1 | 1/2003 | Raz | |
| 2003/0023137 A1 | 1/2003 | Gellman | |
| 2003/0023138 A1 | 1/2003 | Luscombe | |
| 2003/0036676 A1 | 2/2003 | Scetbon | |
| 2003/0045774 A1 | 3/2003 | Staskin et al. | |
| 2003/0050530 A1 | 3/2003 | Neisz et al. | |
| 2003/0065246 A1 | 4/2003 | Inman et al. | |
| 2003/0065402 A1 | 4/2003 | Anderson et al. | |
| 2003/0130670 A1 | 7/2003 | Anderson et al. | |
| 2003/0149440 A1 | 8/2003 | Kammerer et al. | |
| 2003/0176762 A1 | 9/2003 | Kammerer | |

2003/0199732 A1 10/2003 Suslian et al.

FOREIGN PATENT DOCUMENTS

| | | |
|---|---|---|
| DE | 43 04 353 A1 | 4/1994 |
| DE | 4220283 C2 | 5/1994 |
| DE | 101 38 950 | 2/2003 |
| DE | 102 11 360 | 10/2003 |
| EP | 0 470 308 A1 | 2/1992 |
| EP | 0 650 703 A1 | 6/1994 |
| EP | 0 643 945 A2 | 7/1994 |
| EP | 1 093 758 A1 | 4/2001 |
| SU | 1225547 A1 | 4/1986 |
| SU | 1342486 A | 10/1987 |
| WO | WO 93/17635 A1 | 9/1993 |
| WO | WO 93/19678 A2 | 10/1993 |
| WO | WO 97/16121 | 9/1997 |
| WO | WO 98/19606 A1 | 5/1998 |
| WO | WO 98/35606 | 8/1998 |
| WO | WO 98/35616 A1 | 8/1998 |
| WO | WO 98/35632 | 8/1998 |
| WO | WO 99/52450 A1 | 10/1999 |
| WO | WO 00/13601 A1 | 3/2000 |
| WO | WO 00/18319 A1 | 4/2000 |
| WO | WO 00/57812 A1 | 10/2000 |
| WO | WO 00/64370 A1 | 11/2000 |
| WO | WO 00/74594 A1 | 12/2000 |
| WO | WO 00/74613 A1 | 12/2000 |
| WO | WO 00/74633 A2 | 12/2000 |
| WO | WO 01/26581 A1 | 4/2001 |
| WO | WO 01/39670 A1 | 6/2001 |
| WO | WO 01/45589 A1 | 6/2001 |
| WO | WO 01/56499 A1 | 8/2001 |
| WO | WO 01/78609 | 10/2001 |
| WO | WO 02/02031 | 1/2002 |
| WO | WO 02/26108 | 4/2002 |
| WO | WO 02/28312 A1 | 4/2002 |
| WO | WO 02/32284 A2 | 4/2002 |
| WO | WO 02/34124 A2 | 5/2002 |
| WO | WO 02/39890 A2 | 5/2002 |
| WO | WO 02/069781 | 9/2002 |
| WO | WO 02/071953 A2 | 9/2002 |
| WO | WO 02/078552 A1 | 10/2002 |
| WO | WO 2004/016196 A2 | 2/2004 |
| WO | WO 2004/019786 | 3/2004 |

OTHER PUBLICATIONS

U.S. Appl. No. 60/356,697, filed Feb. 14, 2002, Kammerer.
Pelosi II, et al., "New transobturator sling reduces risk of injury", Jul. 2003, 10 pages.
*AMS Monarc subfascial hammock Instructions for Use*, Nov. 2003, English version, 9 pages.
"*Safyre and Transobturator*", DVD, American Medical Systems, Inc., Created Aug. 6, 2001, Modified Sep. 11, 2002.
*Gynecare TVT*, "Tension-Free Support for Incontinence" Marketing Material, Gynecare Worldwide (Feb. 2002), 6 pages.
Sender Hershorn, M.D. et al., "Gynecare TVT With Abdominal Guides Early Clinical Experience" *Gynecare TVT*, Marketing Material, Gynecare Worldwide (May 2002), 12 pages.
Sabre, "Generation Now" *Mentor*, Marketing Material (May 2002), 4 pages.
Safyre, "The Essence of a Contemporary Synthetic Sling—Self-Anchoring Complete Adjustability Elastic" *Promedon*, Marketing Material (Jan. 2002), 4 pages.
Porges U.K. Ltd., "Uratape Perineal Hammock Urethral Support Tape—New Generation of Tape Perineal Implantation" *Mentor*, Marketing Material (Jan. 2002), 6 pages.
Boston Scientific Microvasive, "Precision Twist Transvaginal Anchor System—Low Profile Design for Precise Anchor Placement" *Boston Scientific Corp.*, Marketing Material (2000), 2 pages.
Boston Scientific Microvasive, "Precision Tact Transvaginal Anchor System—The Precise Approach to Transvaginal Sling Procedures" *Boston Scientific Corp.*, Marketing Material (1998), 4 pages.
Boston Scientific Microvasive, "Vesica Sling Kits with Press-In Percutaneous Anchor System—Simplifying Sling Procedures" *Boston Scientific Corp.*, Marketing Material (1998), 4 pages.
"T-Sling (Totally Tension-free) Urinary Incontinence Procedure" *Herniamesh USA Inc.*, Marketing Material (Jan. 2000), 2 pages.
"Advantage A/T—Surgical Mesh Sling Kit", *Boston Scientific-Corp.*, Marketing Material (2002) 1 page.
"Durasphere—Injectable Bulking Agent", *Boston ScientificCorp.*, Marketing Material (2002) 1 page.
"Precision SpeedTac—Transvaginal Anchor System", *Boston ScientificCorp.*, Marketing Material (2002) 1 page.
Boston Scientific Microvasive, "Stone Cone—Nitinol Urological Retrieval Coil", *Boston ScientificCorp.*, Marketing Material (2002) 1 page.
"Swiss LithoClast Ultra—Combination Ulrasonic and Pneumatic Urological Lithotriptor", *Boston ScientificCorp.*, Marketing Material (2002) 1 page.
Boston Scientific Microvasive, "Polaris—Dual Durometer Percuflex Ureteral Stent with HydroPlus Coating", *Boston ScientificCorp.*, Marketing Material (2001) 1 page.
G. A. J. McIndoe et al., National Women's Hospital, Auckland, "The Aldridge Sling Procedure in the Treatment of Urinary Stress Incontinence" Aust NZ J Obstet Gynaecol, 1987; 27: 238.
Charles F. McKlel, Jr. et al., "Marshall-Marchetti Procedure: Modification" *1st Journal in Urology*, vol. 96, pp. 737-739, Nov. 1966, The Williams & Wilkins Co.
Valenzio C. Mascio, M.D., "Therapy of Urinary Stress Incontinence in Women Using Mitek GII Anchors" *Mitek Surgical Products, Inc.*, 5 pages (1993).
Edward J. McGuire, et al., "Pubovaginal Sling Procedure for Stress Incontinence" *The Journal of Urology*, vol. 119, pp. 82-84, Jan. 1978, The Williams & Wilkins Co.
Edward J. McGuire, M.D., "Abdominal Procedures for Stress Incontinence" Symposium on Female Urology, *Urologic Clinics of North America*—vol. 12, No. 2, pp. 285-290, May 1985.
Kevin R. Loughlin, et al., "Review of an 8-Year Experience With Modifications of Endoscopic Suspension of the Bladder Neck for Female Stress Urinary Incontinence" *The Journal of Urology*, vol. 143, pp. 44-45, Jan. 1990 The American Urological Association, Inc.
Irvin L. Lichtenstein, M.D., et al., "The Tension-Free Hernioplasty" *The American Journal of Surgery*, vol. 157, Feb. 1989, pp. 188-193.
Andrew Korda, et al., "Experience with Silastic Slings for Female Urinary Incontinence" *Aust NZ J Obstet Gynaecol*, 1989, vol. 29, pp. 150-154.
Mickey M. Karram, M.D. et al., "Patch Procedure: Modified Transvaginal Fascia Lata Sling for Recurrent or Severe Stress Urinary Incontinence" *Obstetrics & Gynecology*, vol. 75, No. 3, Part 1, Mar. 1990, pp. 461-646.
J. Kersey, "The gauze hammock sling operation in the treatment of stress incontinence" *British Journal of Obstetrics and Gynaecology*, vol. 90 pp. 945-949, Oct. 1983.
A. Ingelman-Sundberg, et al., "Surgical Treatment of Female Urinary Stress Incontinence" *Contr. Gynec. Obstet.* vol. 10, pp. 51-69 (Karger. Basel 1983).
C. Paul Hodgkinson, M.D., et al., "Urinary Stress Incontinence in the Female—III. Round-ligament technic for retropubic suspension of the urethra" *Obstetrics and Gynecology*, vol. 10, No. 5, Nov. 1957, pp. 493-499.
L. Henriksson, M.D. et al., "A urodynamic evaluation of the effects of abdominal urethrocystopexy and vaginal sling urethroplasty in women with stress incontinence" *Am. J. Obstet. Gynecol*, May 1, 1978, pp. 77-82.
Victoria L. Handa, M.D. et al., "Banked Human Fascia Lata for the Suburethral Sling Procedure: A Preliminary Report" *Obstetrics and Gynecology*, vol. 88, No. 6, May 20, 1996, pp. 1045-1049.

C. Falconer, et al., "Influence of Different Sling Materials on Connective Tissue Metabolism in Stress Urinary Incontinent Women" *International Urogynecology Journal*, (2001) (Supp. 2) pp. S19-S23.

H. Enzelsberger et al., "Urodynamic and Radiologic Parameters Before and After Loop Surgery for Recurrent Urinary Stress Incontinence" *Acta Obstet Gynecol Scand 1990*; 69 pp. 51-54.

Bjarne C. Eriksen, et al., "Long-Term Effectiveness of the Burch Colposuspension in Female Urinary Stress Incontinence" *Acta Obstet Gynecol Scand* 1990; 69 pp. 45-50.

John O. L. DeLancey, M.D., "Structural support of the urethra as it relates to stress urinary incontinence: The hammock hypothesis" *Am. J Obstet Gynecol*, pp. 1713-1723, Jun. 1994.

Ross M. Decter, "Use of the Fascial Sling for Neurogenic Incontinence: Lessons Learned" *The Journal of Urology*, vol. 150, pp. 683-686, Aug. 1993, American Urological Association, Inc.

Jong M. Choe, et al., "Gore-Tex Patch Sling: 7 Years Later" *Urology*, 54 (4) pp. 641-646, Apr. 1999, Elsevier Science Inc.

Fred E. Bryans, M.D., F.R.C.S.(C.), "Marlex gauze hammock sling operation with Cooper's ligament attachment in the management of recurrent urinary stress incontinence" *Am. J. Obstet. Gynecol.*, vol. 133, No. 3, pp. 292-294, Feb. 1, 1979.

John C. Burch, M.D., "Urethrovaginal fixation to Cooper's ligament for correction of stress incontinence, cystocele, and prolapse" *Am. J. Obstet. & Gynecol.*, vol. 81 No. 2, pp. 281-290, Feb. 1961.

Jerry G. Blaivas, et al., "Pubovaginal Fascial Sling for the Treatment of Complicated Stress Urinary Incontinence" *The Journal of Urology*, vol. 145, Jun. 1991, pp. 1214-1218, American Urological Association, Inc.

Arieh Bergman, M.D. et al., "Three surgical procedures for genuine stress incontinence: Five-year follow-up of a prospective randomized study", *Am. J. Obstet Gynecol*, vol. 173 No. 1, pp. 66-71, Jul. 1995.

M. Asmussen, et al., "Simultaneous Urethro-Cystometry With a New Technique" *Scand J Urol Nephrol 10*, pp. 7-11, 1976.

Tohru Araki, et al, "The Loop-Loosening Procedure for Urination Difficulties After Stamey Suspension of the Vesical Neck" *The Journal of Urology*, vol. 144, pp. 319-323, Aug. 1990, American Urological Association, Inc.

Peter E. Papa Petros et al., "The Role of a Lax Posterior Vaginal Fornix in the Causation of Stress and Urgency Symptoms: A Preliminary Report" *Acta Obstet Gynecol Scand.*, 69 Suppl. 153, pp. 71-73, 1990.

Peter E. Papa Petros et al., "The Tethered Vagina Syndrome, Post Surgical Incontinence and I-Plasty Operation for Cure" *Acta Obstet Gynecol Scand*. pp. 63-67, 69 Suppl. 153, 1990.

Peter E. Papa Petros et al., "The Tuck Procedure: A Simplified Vaginal Repair for Treatment of Female Urinary Incontinence" *Acta Obstet Gynecol Scand*, 1990, pp. 41-42, 69 Suppl. 153.

Peter E. Papa Petros et al., "The Posterior Fornix Syndrome: A Multiple Symptom Complex of Pelvic Pain and Abnormal Urinary Symtoms Deriving From Laxity in the Posterior Fornix of Vagina" *Scand J Urol Nephrol*, pp. 89-93, Suppl. No. 153, 1993.

Peter E. Papa Petros et al., "The Intravaginal Slingplasty Procedure: IVS VI—further development of the 'double-breasted' vaginal flap repair—attached flap" *Scand J Urol Nephrol*, pp. 81-84, Suppl. No. 153, 1993.

Peter E. Papa Petros et al., "The Further Development of the Intravaginal Slingplasty Procedure: IVS IV—(with "double-breasted" unattached vaginal flap repair and "free" vaginal tapes)" *Scand J Urol Nephrol*, pp. 73-79, Suppl. No. 153, 1993.

Peter E. Papa Petros et al., "The Free Graft Procedure for Cure of the Tethered Vagina Syndrome" *Scand J Urol Nephrol*, pp. 85-87, Suppl. No. 153, 1993.

Peter E. Papa Petros et al., "Pinch Test for Diagnosis of Stress Urinary Incontinence" *Acta Obstet Gynecol Scand*. pp. 33-35, 69 Suppl. 153, 1990.

Peter E. Papa Petros et al., "Pregnancy Effects on the Intravaginal Sling Operation" *Acta Obstet Gynecol Scand*. pp. 73-78, 69 Suppl. 153, 1990.

Peter E. Papa Petros et al., "Part IV: Surgical Applications of the Theory—Development of the Intravaginal Sling Plasty (IVS) Procedure" *Scand J Urol Nephrol*, pp. 53-54, Suppl. No. 153, 1993.

Peter E. Papa Petros et al., "Part III: Surgical Principles Deriving From the Theory" *Scand J Urol Nephrol*, pp. 41-52, Suppl. No. 153, 1993.

Peter E. Papa Petros et al., "Part II: The Biomechanics of Vaginal Tissue and Supporting Ligaments With Special Relevance to the Pathogenesis of Female Urinary Incontinence" *Scand J Urol Nephrol*, pp. 29-40, Suppl. No. 153, 1990.

W. R. Sloan, et al., "Stress Incontinence of Urine: A Retrospective Study of the Complications and Late Results of Simple Suprapubic Suburethral Fascial Slings" *The Journal of Urology*, vol. 110, pp. 533-536, Nov. 1973.

Pat D. O'Donnell, M.D., "Combined Raz Urethral Suspension and McGuire Pubovaginal Sling For Treatment of Complicated Stress Urinary Incontinence" *Journal of The Arkansas Medical Society*, vol. 88, No. 8, pp. 389-392, Jan. 1992.

Nicollette S. Horbach, "Suburethral Sling Procedures" *Urolgynecology and Urodynamics Theory and Practice*, Fourth Edition, Chapter 42, pp. 569-579, 1996, Williams & Wilkins.

Armand J. Pereyra, M.D., F.A.C.S., "A Simplified Surgical Procedure for the Correction of Stress Incontinence in Women" *West J. Surg. Obst. & Gynec.* pp. 223-226, Jul.-Aug. 1959.

M. Asmussen, et al., "Simultaneous Urethro-Cystometry With a New Technique" *Scand J Urol Nephrol 10*, pp. 7-11, 1976.

P. E. Papa Petros "Development of Generic Models for Ambulatory Vaginal Surgery—Preliminary Report" *International Urogynecology Journal*, 9 pages (1998).

Peter E. Papa Petros et al., "An analysis of rapid pad testing and the history for the diagnosis of stress Incontinence" *Acta Obstet Gynecol Scand 71*, pp. 529-536 (1992).

Peter E. Papa Petros et al., "An Integral theory of female urinary incontinence—Experimental and clinical considerations" *Acta Obstet Gynecol Scand*, vol. 69, Suppl. 153, pp. 7-31 (1990), The Scandinavian Association of Obstetricians and Gynecologists.

Rafael F. Nickel et al., "Evaluation of a Transpelvic Sling Procedure With and Without Colposuspension for Treatment of Female Dogs With Refractory Urethral Sphincter Mechanism Incompetence" *Veterinary Surgery*, vol. 27, pp. 94-104, (1998), The American College of Veterinary Surgeons.

Peter E. Papa Petros et al., "Bladder Instability in Women: A Premature Activation of the Micturition Reflex" *Neurology and Urodynamics*, vol. 12, pp. 235-238 (1993).

Peter E. Papa Petros et al., "Cough Transmission Ratio: An Indicator of Suburethral Vaginal Wall Tension Rather Than Urethral Closure?" *Acta Obstet Gynecol Scand*, vol. 69 Suppl. 153. pp. 37-39 (1990).

Jeffrey R. Woodside, et al., "Suprapubic Endoscopic Vesical Neck Suspension for the Management of Urinary Incontinence in Myelodysplastic Girls" *The Journal of Urology*, vol. 135, pp. 97-99, Jan. 1986.

Robert F. Zacharin, FRCS, FRCOG, et al, "Pulsion Enterocele: Long-Term Results of an Abdominoperineal Technique" *Obstetrics & Gynecology*, pp. 141-148, vol. 55, No. 2, Feb. 1980, The American College of Obstetricians & Gynecologists.

Robert F. Zacharin, "The suspensory mechanism of the female urethra" *Journal of Anatomy*, vol. 97, Part 3, pp. 423-427, (1963).

Peter E. Papa Petros et al., "Cure of Stress Incontinence by Repair of External Anal Spincter: Two Case Reports" *Acta Obstet Gynecol Scand*, vol. 69 Suppl. 153, p. 75 (1990).

Peter E. Papa Petros et al., "Cure of Urge Incontinence by the Combined Intravaginal Sling and Tuck Operation" *Acta Obstet Gynecol Scand*, vol. 69 Suppl. 153, pp. 61-62 (1990).

Peter E. Papa Petros et al., "Further Development of the Intravaginal Slingplasty Procedure—IVS III—(with midline "tuck")" *Scand J Urol Nephrol*, Suppl. 153, pp. 69-71 (1993).

Peter E. Papa Petros, "Medium-term Follow-up of the Intravaginal Slingplasty Operation Indicates Minimal Deterioration of Urinary Continence With Time" *International Urogynecology Journal and Pelvic Floor Dysfunction*, Reprinted from vol. 7, No. 3, pp. 133-137, (1996).

Peter E. Papa Petros et al., "Non Stress Non Urge Female Urinary Incontinence—Diagnosis and Cure: A Preliminary Report" *Acta Obstet Gynecol Scand*, vol. 69 Suppl. 153. pp. 69-70 (1990).

Shlomo Raz, M.D., "Modified Bladder Neck Suspension for Female Stress Incontinence" *Urology*, vol. XVII, No. 1, pp. 82-85, Jan. 1981, University of California Health Sciences Center, Los Angeles, CA.

David A. Richardson, M.D., et al., "Delayed Reaction to the Dacron Buttress Used in Urethropexy" *The Journal of Reproductive Medicine*, vol. 29 No. 9, Sep. 1984, pp. 689-692.

Henry Roberts, M.D., M.R.C.O.G., "Cystourethrography in Women" *Ethel Bovce University Fellowship* vol. 25 No. 293, pp. 253-259, May 1952, University of Liverpool.

W. R. Sloan et al., "Stress Incontinence of Urine: A Retrospective Study of the Complications and Late Results of Simple Suprapubic Suburethral Fascial Slings", *The Journal of Urology*, vol. 110, pp. 533-536, Nov. 1973.

Julie R. Spencer, et al., "A Comparison of Endoscopic Suspension of the Vesical Neck With Suprapubic Vesicourethropexy for Treatment of Stress Urinary Incontinence" *The Journal of Urology*, vol. 137, pp. 411-415, Mar. 1987.

Stuart L. Stanton, FRCS, FRCOG, "Suprapubic Approaches for Stress Incontinence in Women" *JAGS*, vol. 38, No. 3, pp. 348-351 (1990), The American Geriatrics Society.

Ulf Ulmsten et al., "Different Biochemical Composition of Connective Tissue In Continent and Stress Incontinent Women" *Acta Obstet Gynecol Scand*, vol. 66 pp. 455-457 (1987).

Ulf Ulmsten et al., "The unstable female urethra" *Am. J. Obstet. Gynecol.*, vol. 144 No. 1, pp. 93-97, May 3, 1982.

U. Ulmsten, "Female Urinary Incontinence—A Symptom, Not a Urodynamic Disease. Some Theoretical and Practical Aspects on the Diagnosis and Treatment of Female Urinary Incontinence" *The International Urogynecology Journal*, vol. 6, pp. 2-3 (1995).

Peter Papa Petros et al., "Anchoring the midurethra restores bladder-neck anatomy and continence" *The Lancet*, vol. 354, pp. 997-998, Sep. 18, 1999.

Edward J. McGuire, et al., "Experience With Pubovaginal Slings for Urinary Incontinence at the University of Michigan" *The Journal of Urology*, vol. 138, pp. 525-526, Sep. 1987.

G. Narik, M.D., "A simplified sling operation suitable for routine use" *The Am J. Obst. & Gynec.*, vol. 84, No. 3, pp. 400-405, Aug. 1, 1962.

Chester C. Winter, M.D., "Peripubic Urethropexy for Urinary Stress Incontinence in Women" *Urology* vol. XX, No. 4, Oct. 1982.

J. Chassar Moir, "The Gauze-Hammock Operation (A Modified Aldridge Sling Prcedure)" *The Journal of Obstetrics and Gynaecology of the British Commonwealth*, vol. 75 No. 1, pp. 1-9, Jan. 1968.

George D. Webster, et al., "Voiding Dysfunction Following Cystourethropexy: Its Evaluation and Management" *The Journal of Urology*, vol. 144, Sep. 1990,pp. 670-673, American Urological Association, Inc.

J. E. Morgan, M.D., "A sling operation, using Marlex polypropylene mesh, for treatment of recurrent stress incontinence" *Amer. J. Obstet. Gynec.* vol. 106, No. 3, Feb. 15, 1970, pp. 369-377.

David H. Nichols, MD, FACOG, "The Mersilene Mesh Gauze-Hammock For Severe Urinary Stress Incontinence" *Obstetrics and Gynecology*, vol. 41, No. 1, pp. 88-93, Jan. 1973.

Jeffrey P. Norris, M.D., et al., "Use of Synthetic Material in Sling Surgery: A Minimally Invasive Approach" *Journal of Endourology*, vol. 10 No. 3, pp. 227-230, Jun. 1998, Mary Ann Liebert, Inc.

Peter Papa Petros et al., "The Autogenic Ligament Procedure: A Technique for Planned Formation of an Artificial Neo-Ligament" *Acta Obstet Gynecol Scand*, vol. 69 Suppl 153, pp. 43-51 (1990).

Peter Papa Petros et al., "The Combined Intravaginal Sling and Tuck Operation. An Ambulatory Procedure for Cure of Stress and Urge Incontinence" *Acta Obstet Gynecol Scand*, vol. 69 Suppl 153, pp. 53-59 (1990).

Peter Papa Petros et al., "Urethral Pressure Increase on Effort Originates From Within the Urethra, and Continence From Musculovaginal Closure" *Neurourology and Urodynamics*, vol. 14, pp. 337-350 (1995).

R. O. Parra, et al., "Experience with a Simplified Technique for the Treatment of Female Stress Urinary Incontinence" *British Journal of Urology*, vol. 66, pp. 615-617 (1990).

Raymond R. Rackley, M.D., et al. "Tension-free Vaginal Tape and Percutaneous Vaginal Tape Sling Procedures" *Techniques in Urology*, vol. 7, No. 2, pp. 90-100 (2001).

Raymond Rackley, M.D., "Synthetic slings: Five steps for successful placement" *Urology Times*, pp. 46, 48-49, Jun. 2000.

Shlomo Raz, M.D. et al., "Female Urology—Second Edition" *University of California at Los Angeles School of Medicine*, articles pp. 80-86, 369-381, 382-391, 392-394, 395-398, 435-442, (1983) W.B. Saunders Company.

John H. Ridley, M.D., "Appraisal of the Goebell-Frangenheim-Stoeckel sling procedure" *Am. J. Obst. & Gynec.* vol. 95, No. 5, pp. 714-721, Jul. 1, 1966.

Thomas A. Stamey, M.D., "Endoscopic Suspension of the Vesical Neck for Urinary Incontinence in Females" *Ann Surg.*, vol. 192, No. 4, pp. 465-471, Oct. 1980.

David R. Staskin, et al., "The Gore-tex sling procedure for female sphincteric incontinence: indications, technique, and results" *World J Urol.*, 1997, vol. 15, pp. 295-299 , Springer-Verlag.

Gynecare, *TVT*—"Tension-Free Vaginal Tape, Minimally Invasive, Highly Effective Treatment for Female Stress Urinary Incontinence" Marketing Brochure, *Ethicon, Inc.* (1999) 6 pages.

U. Ulmsten et al., "A Multicenter Study of Tension-Free Vaginal Tape (TVT) for Surgical Treatment of Stress Urinary Incontinence" *The International Urogynecology Journal*, 1998, vol. 9, pp. 210-213.

U. Ulmsten et al., "A three-year follow up of tension free vaginal tape for surgical treatment of female stress urinary incontinence" *The British Journal of Obstetrics and Gynaecology*, Apr. 1999, vol. 106, pp. 345-350.

U. Ulmsten et al., "An Ambulatory Surgical Procedure Under Local Anesthesia for Treatment of Female Urinary Incontinence" *The International Urogynecology Journal*, 1996, vol. 7, pp. 81-86.

U. Ulmsten et al., "Intravaginal Slingplasty (IVS): An Ambulatory Surgical Procedure for Treatment of Female Urinary Incontinence" *Scand J Urol Nephrol*,vol. 29 pp. 75-82, 1995, Scandinavian University Press ISSN.

C. Falconer et al., "Clinical Outcome and Changes in Connective Tissue Metabolism After Intravaginal Slingplasty in Stress Incontinent Women" *International Urogynecol J*, vol. 7, pp. 133-137, (1996).

Ruben F. Gittes et al, "No Incision Pubovaginal Suspension for Stress Incontinence" *The Journal of Urology*, vol. 138, pp. 568-570, Sep. 1987.

John Klutke, M.D. et al., "The promise of tension-free vaginal tape for female SUI" *Focus on Technology 2000*, pp. 59-60, 65-66, 69-70, 73, Oct. 2000, *Contemporary Urology*.

Urogynecology, Product Catalog, eg. SIS Technology, Bladder Suspension, Urodynamics and Urinary Diversion, Incontinence, 36 pages, Cook, Urological Inc. (1996).

Theodore V. Benderev. M.D., "Anchor Fixation and Other Modifications of Endoscopic Bladder Neck Suspension" *Urology*, vol. 40, No. 5, pp. 409-418, Nov. 1992.

Martin, Surgical Products Catalog, 8 pages, Martin Medizin-Technik, Gebrüder Martin GmbH & Co. KG (1998).

Beck, Peter R. et al., Treatment of Urinary Stress Incontinence With Anterior Colporrhaphy. Obstetrics and Gynecology, vol. 59 (No. 3), pp. 269-274 (Mar. 1982).

Benderev, Theodore V., MD, A Modified Percutaneous Outpatient Bladder Neck Suspension System, Journal of Urology, vol. 152, pp. 2316-2320 ldec. 1994).

Das, Sakti et al., Laparoscopic Colpo-Suspension, The Journal of Urology, vol. 154, pp. 1119-1121 (Sep. 1995).

Gija, Ivan et all, A Modified Raz Bladder Neck Suspension Operation (Transvaginal Burch), The Journal of Urology, vol. 153, pp. 1455-1457 (May 1995).

Holschneider, C.H., et al., The Modified Pereyra Procedure in Recurrent Stress Urinary Incontinence: A 15-year Review, obstetrics & Gynecology, vol. 83, No. 4, pp. 573-578 (Apr. 1994).

Horbach, Nicollette S., et al., Instruments and Methods, A Suburethral Sling procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).

Klutke, Carl et al., The Anatomy of Stress Incontinence: Magentic Resonance Imaging of the Female Bladder Neck and Urethra, The Journal Urology, vol. 143, pp. 563-566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).

Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).

Leach, Gary E., et al, Female Stress Urinary Incontinence Clinical Guidelines Panel Report on Surgical Management of Female Stress Urinary Incontinence, American Urological Association, vol. 158, pp. 875-880 (Sep. 1997).

Leach, Gary E., MD, Bone Fixation Technique for Transvaginal Needle Suspension, Urology vol. XXXI, No. 5, pp. 388-390 (May 1988).

McGuire, Edward J. et al., Experience With Pubovaginal Slings for Urinary Incontinence at the University of Michigan, Journal of Urology, vol. 138, pp. 90-93(1987).

McGuire, Edward J. et al., Abdominal Fascial Slings, Slings, Raz Female Urology, pp. 369-375 (1996).

Morgan, J.E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advanced Surgical Techniques, vol. 9, No. 1 pp. 45-50 (1999).

Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).

Petros, Peter E. Papa et al., Part IV: Surgical Applications of the Theory-Development of the Intravaginal Sling Plasty (IVS) Procedure, Scandinavian Journal of Neurology and Urodynamics, Sup 153, pp. 53-54 (1993).

Stanton, Stuart, Springer-Verlag, Surgery of Female Incontinence, pp. 105-113 (1986).

Staskin, David R. et al., The Gore-Tex Sling Procedure for Female Sphincteric Incontinence: Indications, Technique, and Results, World Journal of Urology, vol. 15, pp. 295-299 (1997).

TVT Tension-free Vaginal Tape, Gynecare, Ethicon, Inc., 23 pages (1999).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93-100, vol. 21 (Mar. 1996).

Zimmern, Phillippe E. et al., Four-Corner Bladder Neck Suspension, Vaginal Surgery for the Urologist, vol. 2, No. 1, pp. 29-36 (Apr. 1994).

Mentor-Porges, Trans-obturator tape, Le hamac perinial, Nos references, Marketing Material in French language, 1 page (Jan. 2003).

Mentor-Porges, Come See Us at Booth #28, Marketing Material, 1 page (Jul. 2002).

Mentor, Sabre™ Bioabsorbable Sling, Surgical Procedure, Marketing Material, 6 pages, (Aug. 2002).

Raz, Shlomo, et al., The Rax Bladder Neck Suspension Results in 206 Patients, The Journal of Urology, pp. 845-850 (Sep. 1992).

Marco A. Pelosi II, et al., New Tranobturator Sling Reduces Risk of Injury, OBG Management , pp. 17-20, 30, 32, 35-38 (Jul. 2003).

Dargent, D., et al. Pose d'un ruban sous uretral oblique par vole obturatrice dans le traitement de l'Incontinence urinaire feminine, Gynecol Obstet Fertil 2002; 30: 576-582 (2002) (Provided in both French and English languages), 13 pages.

de Leval, Jean "Novel Surgical Technique for the Treatment of Female Stress Urinary Incontinence: Transobturator Vaginal Tape Inside-Out", European Urology 44 (2003) 724-730.

Delorme, Emmanuel et al., "Transobturator Tape (Uratape®): A New Minimally-Invasive Procedure to Treat Female Urinary Incontinence", European Urology 45 (2004) 203-207.

Letters To The Editor , R. Villet's response to the article by D. Dargent et al., "Placement of an obilque transobturator suburethral tape in the treatment of female urinary incontinence", Gynecology Obstetrics & Fertility 31 (2003) 96-101 (English Translation).

H.P. Dietz et al., "Mechanical Properties of urogynecologic Implant Materials", International urogynecology Journal (2003) 14:239-243.

C.B. Iglesia et al., "The Use of Mesh in Gynecologic Surgery", International Urogynecology Journal (1997) 8:105-115, © 1997 Springer-Verlag London Ltd.

C.C. Chu and L. Welch, "Characterization of Morphologic and Mechanical Properties of Surgical Mesh Fabrics", Journal of Biomedical Materials Research, vol. 19, 903-916 (1985), © 1985 John Wiley & Sons, Inc.

J.E. Morgan, M.D., "A sling operation, using Marlex Polypropylene mesh, for treatment of recurrent stress incontinence", American Journal of Obstetrics and Gynecology, Feb. 15, 1970, 106:3, pp. 369-377.

J.E. Morgan, M.D. et al., "The Marlex sling operation for the treatment of recurrent stress urinary incontinence: A 16-year review", American Journal of Obstetrics and Gynecology, Jan. 15, 1985, pp. 224-227.

Pourdeyhimi, "Porosity of surgical mesh fabrics: New technology", J. Biomed. Mater. Res.: Applied Biomaterials, vol. 23, No. A1, 145-152 (1989), © 1989 John Wiley & Sons, Inc.

"Urinary Incontinence: Easier Operation", Article from la Libre Belgique, Wednesday, Oct. 15, 2003 (English Translation).

Delorme, "La bandelette trans-obturatrice: un procede mini-invasif pour traiter l'Incontinence urinaire d'effort de la femme", Urologie de la Femme, 2001:11, pp. 1306-1313 with English Translation.

* cited by examiner

HANDLE AND SURGICAL ARTICLE

CROSS REFERENCE TO RELATED APPLICATIONS

The present application is a continuation in part of U.S. Utility application Ser. No. 10/386,897, filed Mar. 11, 2003 now abandoned and U.S. Utility application Ser. No. 10/306,179, filed Nov. 27, 2002 now U.S. Pat. No. 7,070,556; which '897 and '179 applications claim the benefit of U.S. Provisional Application Ser. No. 60/362,806, filed Mar. 7, 2002; and U.S. Provisional Application Ser. No. 60/380,797, filed May 14, 2002; and U.S. Provisional Application Ser. No. 60/402,007, filed Aug. 8, 2002; and U.S. Provisional Application Ser. No. 60/414,865 filed Sep. 30, 2002. The entire contents of all of the previous patent applications are herein incorporated by reference.

BACKGROUND

There are a wide variety of surgical instruments used in procedures for treating pelvic floor disorders. Needles, suture passers and ligature carriers are commonly available in surgical centers and hospitals. Examples of such surgical instruments include Stamey needles, Raz needles, and Pereyra needles. See Stamey, *Endoscopic Suspension of the Vesical Neck for Urinary Incontinence in Females*, Ann. Surgery, pp. 465-471, October 1980; and Pereyra, *A Simplified Surgical Procedure for the Correction of Stress Incontinence in Women*, West. J. Surg., Obstetrics & Gynecology, pp. 243-246, July-August 1959.

Handles used with surgical instruments for treating pelvic floor disorders vary in size and shape. U.S. Pat. Nos. 5,112,344; 5,899,909; 6,605,097 and 6,612,977 show various handles for use with surgical instruments for treating pelvic floor disorders such as incontinence. Published U.S. Pat. Application No. 2002 0099259-A1 discloses a handle for use with a needle useful in a variety of procedures, including a sling procedure for treating incontinence. Other handles are disclosed in published U.S. Pat. Application Nos. 2002 091298-A1 and 2001 0053916-A1.

Emmett needles are used in procedures for treating incontinence. An Emmet needle is depicted in Dargent et al., *Pose d'un ruban sous uretral oblique par voie obturatrice dans le traitement de l'incontinence urinaire feminine*, Gynecol. Obstet. Fertil 2002; 30:576-82. The Emmet needle includes a handle, a curved portion with a tip and what can be described as a short, straight portion between the curved portion and the handle. However, the needle is generally not meant to be rotated about the axis of the straight portion while it is within the body.

Some suture passers have straight and curved portions. These suture passers are typically reusable devices with a relatively sharp tip. These devices typically are cast from a relatively heavy metal, such as stainless steel, with no plastic component. As a result, a large proportion of the weight of the reusable suture passers resides in their handle portions.

SUMMARY OF THE INVENTION

In one aspect, the present invention comprises a handle for a surgical instrument having a needle with a substantially straight portion and a curved portion. The handle comprises an elongate body having a proximal end region, a distal end region, a top portion and a bottom portion. The straight portion of the needle is adapted to project from a distal end of the body. The top portion has a substantially flat surface in the distal end region.

Preferably, the proximal end region is non-cylindrical with the width being greater than the height. The proximal end region preferably has generally convex surfaces. At least the top portion preferably has a surface that is sized and shaped to receive a user's thumb in the distal end region. In a preferred embodiment, the proximal end region has a maximum height that is larger than the height of any portion of the distal end region. Also preferably, the body has side portions with a plurality of grasping ribs.

In a preferred embodiment, the distal end region has a maximum width that is greater than the width of any portion of the proximal end region. This structure preferably forms fins.

The handle preferably includes a surface that is sized and shaped to receive a user's thumb. However, it is noted that different surgeons may grasp and use the surgical instrument according to individual preference and the present invention is not limited if a particular surgeon does not utilize a particular surface as a thumb rest.

The elongate body has an elongate axis, and the straight portion of the needle has an elongate axis, and the axis of the elongate body is at least parallel to the axis of the straight portion of the instrument, preferably they are coaxial.

In another aspect, the present invention comprises a handle for a surgical instrument. The surgical instrument has a needle with a substantially straight portion and a curved portion. The handle comprises a proximal end region, a distal end region, and a transition region between the proximal and distal end regions. The maximum height of the transition region is less than the maximum height of the proximal end region. The maximum width of the transition region is less than the maximum width of the proximal end region. The maximum width of the transition region is less than the maximum width of the distal end region.

In another aspect, the present invention comprises a surgical instrument for treating pelvic floor disorders. The surgical instrument comprises a metallic needle portion having a substantially straight portion and a substantially curved portion. The instrument includes a handle portion constructed at least in part from a polymeric material, the handle portion comprising a proximal end region, a distal end region, and a transition region between the proximal and distal end regions. The transition region is reduced in width relative to the proximal and distal end regions.

Preferably, the metallic needle portion has a tip portion that is at least substantially blunt and is constructed from stainless steel. Also preferably, the proximal end region has a maximum height that is greater than the maximum height of the transition region and the maximum height of the distal end region. The transition region has a maximum width that is preferably less than the maximum width of the distal region and the maximum width of the proximal region.

Preferably, the transition region has a substantially concave surface. Also preferably, the length of the proximal region is longer than the combined lengths of the transition region and distal end region. In a preferred embodiment, the distal end region comprises a pair of fins projecting from sides of the handle.

BRIEF DESCRIPTION OF THE DRAWINGS

Other features and advantages of the present invention will be seen as the following description of particular embodiments progresses in conjunction with the drawings, in which.

DETAILED DESCRIPTION

Figure 1:
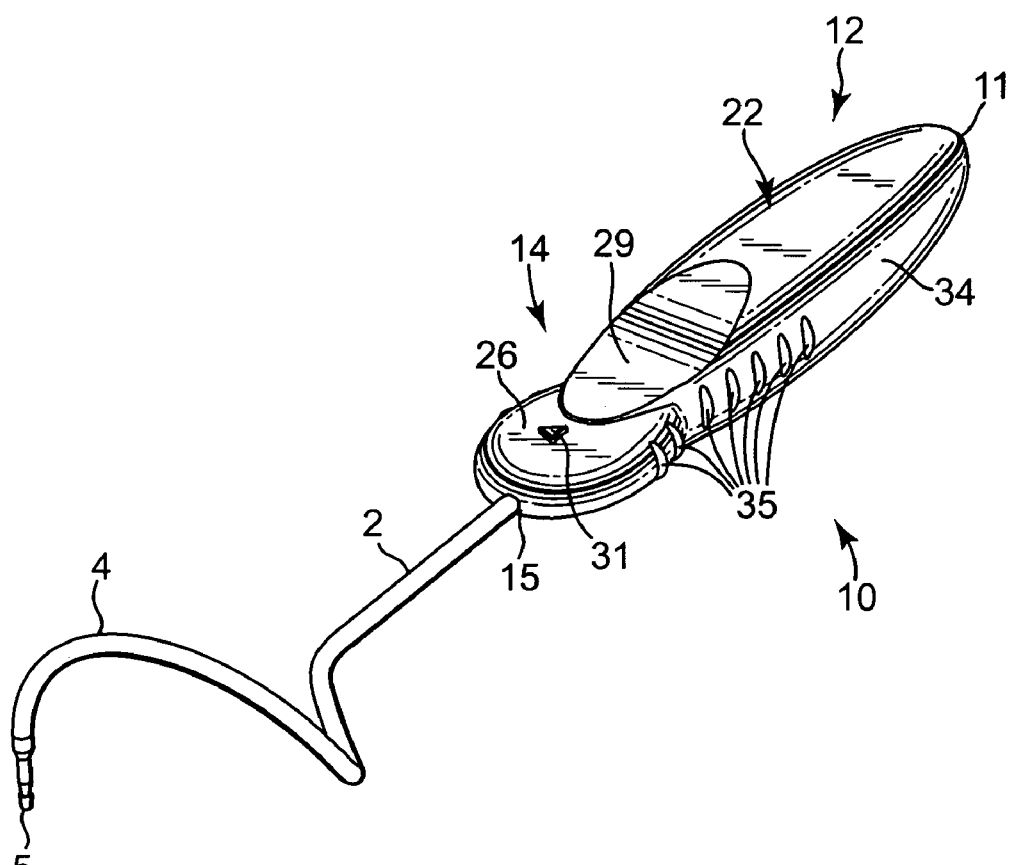
FIG. 1 is a perspective view of a surgical instrument with a handle according to one aspect of the present invention.
Figure 2:
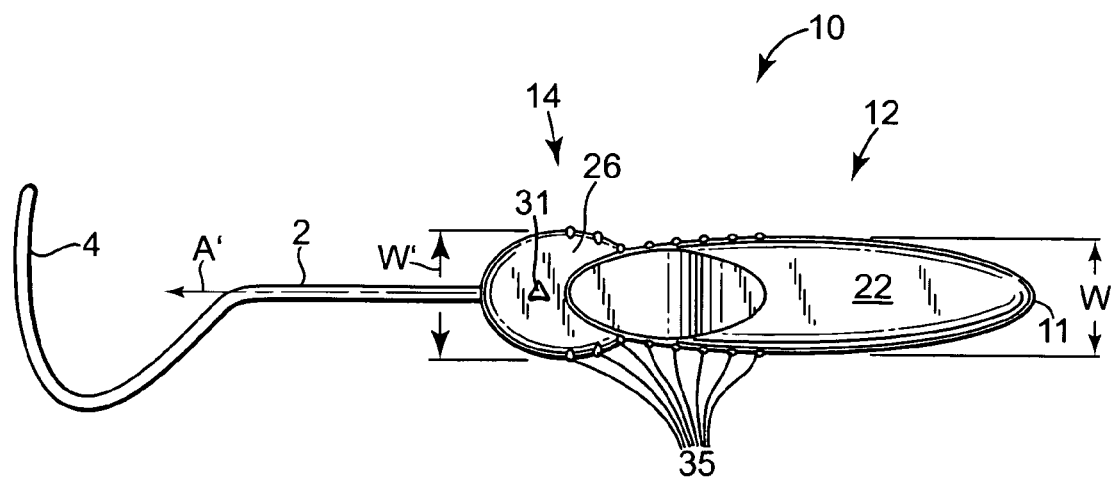
FIG. 2 is a top view of the, surgical instrument of FIG. 1.
Figure 3:
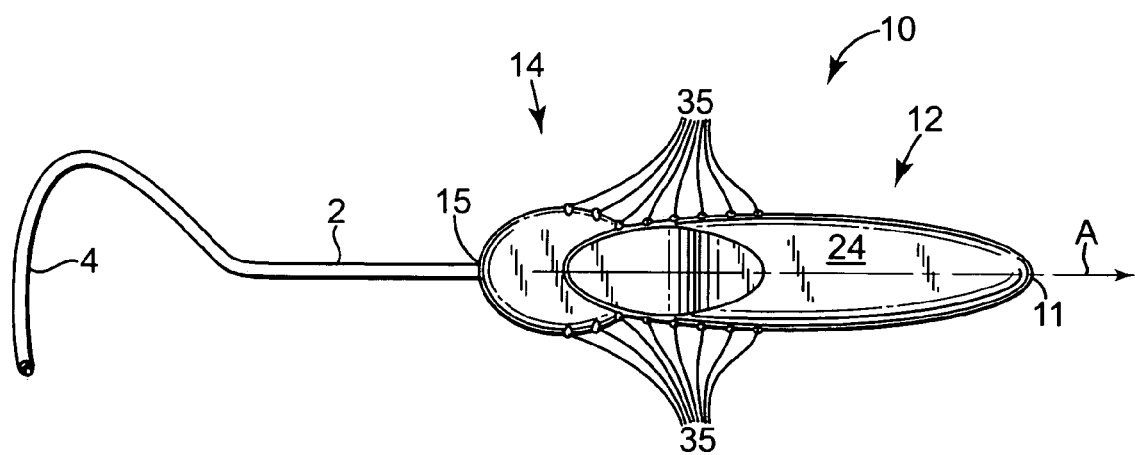
FIG. 3 is a bottom view of the surgical instrument of FIG. 1.
Figure 4:
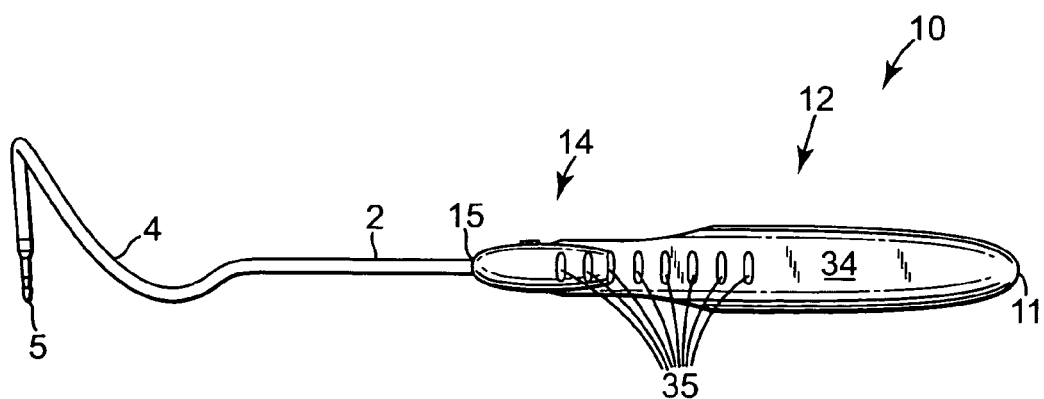
FIG. 4 is a right side view of the surgical instrument of FIG. 1.

The following description is meant to be illustrative only and not limiting. Other embodiments of this invention will be apparent to those of ordinary skill in the art in view of this description.

The present invention is directed to surgical instruments and more particularly handles for surgical instruments used in pelvic floor surgical procedures such as incontinence or stress urinary incontinence (SUI) in both men and women. Although the invention as disclosed herein generally refers to SUI, the surgical instruments may be used for treatment of other urological or gynecological disorders, such as prolapse (e.g. vaginal and uterine), enteroceles (e.g. of the uterus or small bowel), rectoceles, cystoceles and other disorders are also included within the scope of the present invention. The present invention is particularly suitable for use in conjunction with concomitant procedures, such as, but not limited to, procedures for addressing cystocele, rectocele, vaginal prolapse and anatomic corrections. Various pelvic floor procedures and implants for use in such procedures are disclosed in Staskin et al., U.S. patent application Ser. No. 10/423,662 filed, Apr. 25, 2003.

The handles of the present invention are particularly suitable for use with a surgical instrument (e.g. a needle) having a straight portion 2 and a curved portion 4. Such instruments are disclosed in Pelosi II, et al., *New Transobturator Sling Reduces Risk of Injury*, OBG Management, Pps. 17-38 (2003). In use, the curved portion of the needles are preferably passed around the inferior aspect of the ischiopubic ramus. For example, the distal end 5 of the needle may begin tissue passage with penetration of the skin (or incision) and subcutaneous tissue near the patient's obturator foramen. After moving through superficial perineal fascia, the needle may cross adductor muscles of the thigh near their pubic bone origin and below the insertion point of the adductor longus tendon. The needle may then penetrate the obturator membrane, obturator internus muscle, and periurethral endopelvic fascia. After passing the level of the white line, either over or under the puborectalis section of the levator, the distal end 5 of the needle may exit through a vaginal incision. Suitable needles are also disclosed in U.S. Pat. Application Nos. 2003 0212305-A1, 2003 0176875-A1 and 2003 0171644-A1. Preferably the curved portion 4 is helical or spiral shaped and has a tip 5. As an example, not intended to be limiting, to form a right handed helix, a bending mandrel with a groove may be used with dimensions of about 1.56 inches diameter, pitch about 1.85, and a degree of wrap to a bending pin on the mandrel of about 350 degrees. These dimensions are only an example and the present invention contemplates widely varying dimensions. These dimensions are prior to any spring back of the metal, and are believed suitable for a 17-4 stainless steel rod with a circular cross sectional diameter of 3.2 mm. The straight portion of the needle may be, for example, about 20 degrees off the axis of helix axis.

Also as an example not intended to be limiting, the overall maximum width of the finished curved portion may be about 2.15 inches and the bent portion of the needle may have an axial length of about 2 inches.

The tip 5 may be slightly sharpened or blunt. The region near the end of the tip may include an eyelet or it may include surfaces sized and shaped to engage with complementary surfaces on a connector and/or a sling assembly.

Notably, the handles and surgical instruments according to the present invention may be utilized with needles and surgical approaches that initially pass a needle tip through a vaginal incision and then through an incision generally adjacent a patient's obturator foramen. Also, the handles and surgical instruments according to the present invention may be utilized with instruments designed for a specific side of the patient's body (e.g. right or left) or with universal instruments designed for use on either side of the patient's body. Also, the handles and surgical instruments according to the present invention may be utilized with instruments designed for use by a surgeon's dominant hand (e.g. right or left handed). Additionally, the handles may be used with instruments that are initially inserted into the body in one general direction (i.e. a forward or insertion direction), and then removed from the body in a generally opposite direction (i.e. a reverse or removal direction). Alternatively, the surgical instrument may be used as a guide for a sling assembly.

The cross section of the needles may be of any suitable shape, preferably circular. The diameter of the circle is preferably less than about 4.5 mm, more preferably about 3.2 mm or less. The diameter of the needle may be substantially uniform along its length or it may vary. For example, the diameter may be increased at positions of greater stress or rotational bending moment, to increase the resistance of the needle to bending during use.

The tip region 5 preferably includes a reduced diameter portion, but a slightly enlarged portion with an eyelet is also within the scope of the present invention. The tip region optionally has structure for associating the instrument with another surgical article (e.g. a connector, dilator, sling assembly, sling, insertion sleeve or suture). Optionally, the tip region may incorporate specially designed surfaces for cooperating with complementary surfaces on another surgical article, such as the structures described in U.S. Pat. No. 6,641,525 or U.S. Pat. Application Publication No. 2002/0099259, published Jul. 25, 2002 (U.S. patent application Ser. No. 09/917,445, filed Jul. 27, 2001), or U.S. Pat. Application Publication No. 2002/0147382 published Oct. 10, 2002. In an alternative embodiment, an eyelet may be provided in the distal tip region.

A variety of different materials may be used to construct the straight 2 and curved portions 4 of the surgical instrument including, but not limited to medical grade plastics and metals. The straight 2 and curved portions 4 are preferably constructed from a metal. Suitable materials include titanium, stainless steel, other medical grade alloys. Suitable stainless steels include AISI types 316, 3161, 17-4 (e.g. PH H900), 302, 303 and 304.

Referring now to FIGS. 1-7, there is shown a preferred embodiment of handle 10 according to the present invention.

The handle 10 has an elongate body with a proximal end region 12 having a width W, height H and a proximal end 11. The body also has a distal end region 14 with a width W', height H' and a distal end 15, a top portion 22 and a bottom portion 24.

Preferably, the straight portion 2 of the needle projects from the distal end 15 of the body 10, preferably along its longitudinal axis A. Also preferably, the axis A of the elongate body of the handle 10 is substantially coaxial with the axis A' of the straight portion 2 of the needle. A user of the needle may manually place a moment about the axis A' of the needle in a convenient fashion. The handle is particularly suitable for affording passage of the distal end 5 of the needle with a natural wrist rotation. As a result, the position of the tip 5 of the needle may be conveniently controlled. As can be seen by comparing FIGS. 4 and 5, the body 10 is preferably substantially symmetrical about the axis A.

The top portion of the handle has a substantially flat surface 26 in the distal end region 14. The tip 5 of the needle may be required to move very short, substantially straight distances in a controlled manner. For example, the tip 5 may need to traverse a certain type of relatively tough tissue (e.g. the obturator foramen) in a substantially short, linear path just prior to moving along a more complex path. This initial motion is substantially linear and a relatively short distance of the overall intended path for the tip.

The bottom portion 24 also preferably has a substantially flat surface in the distal end region 14. The substantially flat surface on the bottom surface 24 (opposite surface 26) is preferably sized and shaped to exploit forces applied to the handle 10 by a user's thenar muscles. The thenar muscle of the thumb is one of the few power producing muscles in the hand. See Salvendy, *Handbook of Human Factors and Ergonomics*, Second Edition, John Wiley & Sons, Inc. (1997). The handle 10 is preferably sized and shaped to exploit the use of this muscle, for example, during the surgeon's wrist rotation. Notably, other surgeons may use the flat surfaces 26 (and flat surface opposite surface 26, on the bottom 24 of the body 10) for other purposes. The actual grasping of the handle by a particular surgeon is dictated by a variety of factors such as surgeon training, comfort, dexterity, strength, etc.

The distal end region preferably has relatively or substantially flat fins. The distal end region 14 has a maximum width W' that is preferably greater than the width W of any portion of the proximal end region 12. This conveniently allows a user to place a thumb underneath a fin (e.g. on the bottom surface 24 of the handle 10), to rotate the handle about the axis A and place a moment about the axis A' of the straight portion 2 of the instrument. This affords a convenient, controlled movement of the tip 5 of the instrument along its complex (i.e. non-linear) path. As an example of a preferred embodiment of the present invention, the maximum width W' may be between about 0.8 and 1.4 inches, more preferably about 1.2 inches. The maximum width W may be between about 0.7 and 1.3 inches, more preferably about 1.1 inches.

At least the top surface of the proximal end region 12 is preferably at least slightly convex. Preferably, the proximal end region 12 is non-cylindrical. Also preferably, the maximum width of the proximal end region 12 is preferably greater than its maximum height. The proximal end region 12 has a maximum height H that is preferably larger than the height H' of any portion of the distal end region 14. The proximal end region affords a convenient secure grasp in the palm of a user's hand. This convenient grip is believed to afford efficient power transmission to the tip 5, especially during rotation of the body 10. As an example of a preferred embodiment of the present invention, the maximum height H may be between about 0.5 and 1.5 inches, more preferably about 0.7 to 1 inches, more preferably about 0.81 inches. The maximum height H' may be between about 0.25 and 0.65 inches, more preferably about 0.44 inches There may optionally be a transition region between the proximal 12 and distal 14 regions, as shown in FIGS. 2-5. The transition region may be reduced in size (e.g. width) relative to the proximal and distal regions. The overall length of the body 10 may be between 3 and 7 inches. In one embodiment, the length is about five inches. This size of handle is preferred with a needle that has a straight portion length of about 2 inches as measured from the end 15 of the body 10 to the beginning of the curved portion 4. The length of the proximal region 12 is preferably greater than the length the distal region 14 or the transition region.

The body has side portions 34 and 36. The surfaces of the side portions 34 and 36 are preferably substantially concave shaped in the transition region.

Figure 5:
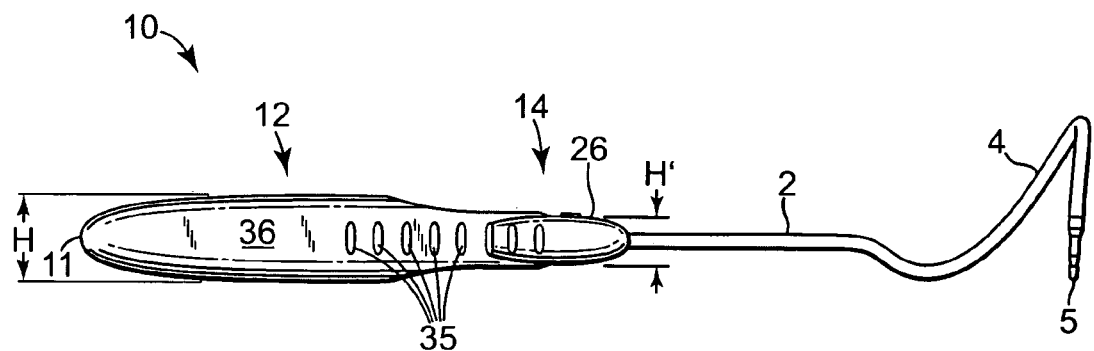
FIG. 5 is a left side view of the surgical instrument of FIG. 1.
Figure 6:
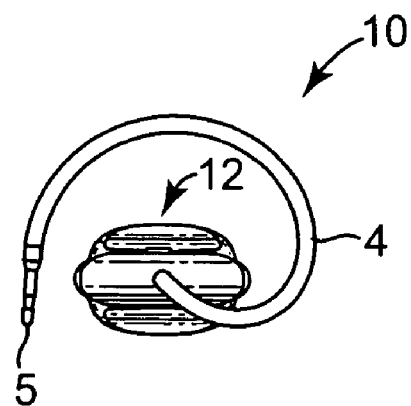
FIG. 6 is a front end view of the surgical instrument of FIG. 1.
Figure 7:
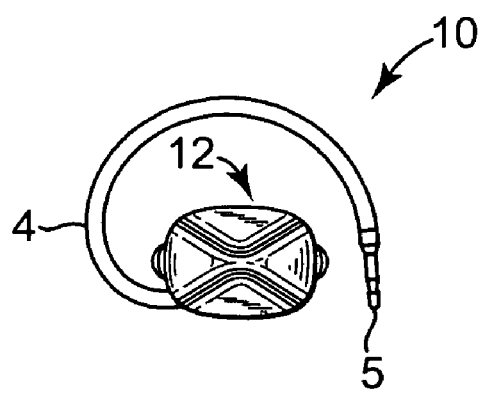
FIG. 7 is a rear end view of the surgical instrument of FIG. 1.
Figure 8:
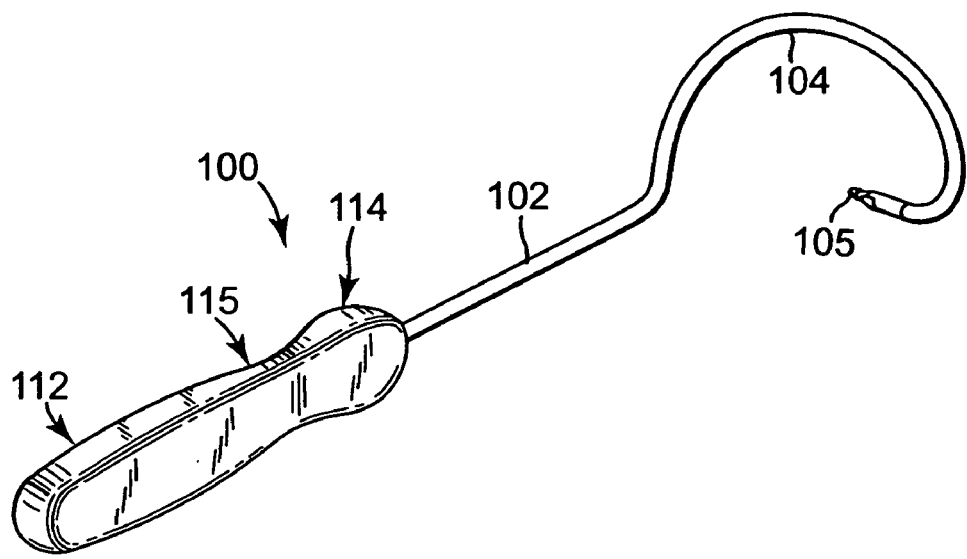
FIG. 8 is a perspective view of another embodiment of surgical instrument according to the present invention.
Figure 9:
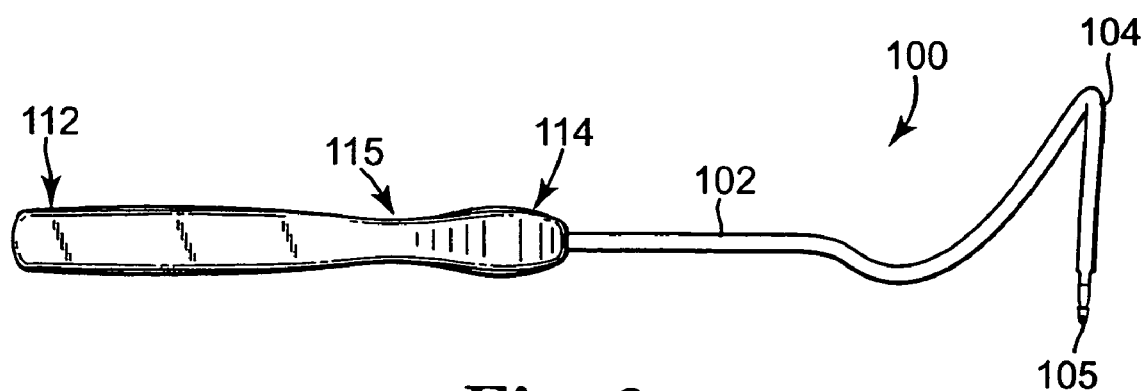
FIG. 9 is a right side view of the instrument of FIG. 8.
Figure 10:
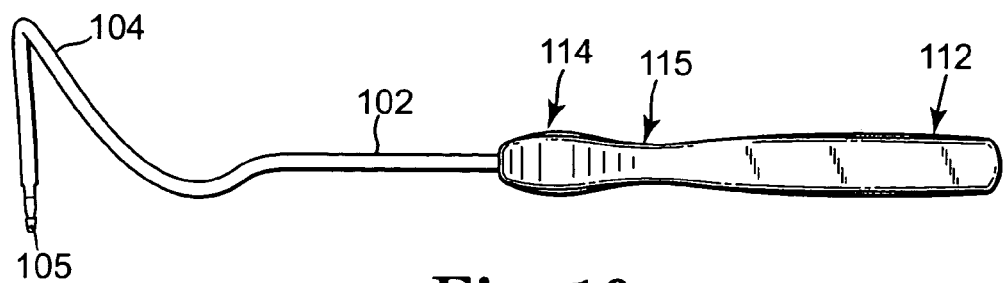
FIG. 10 is left side view of the instrument of FIG. 8.
Figure 11:
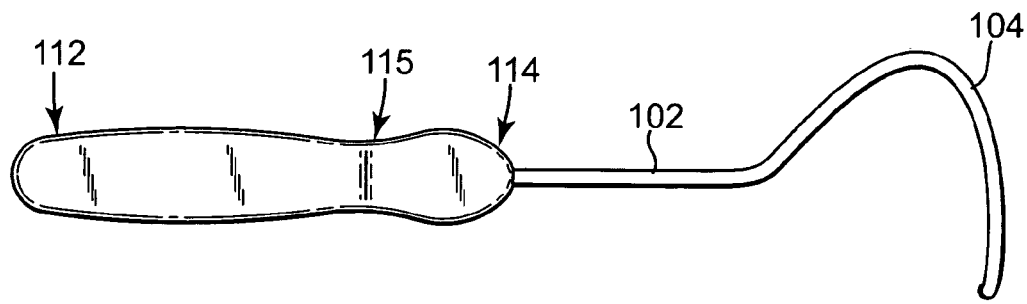
FIG. 11 is a top view of the instrument of FIG. 8.
Figure 12:
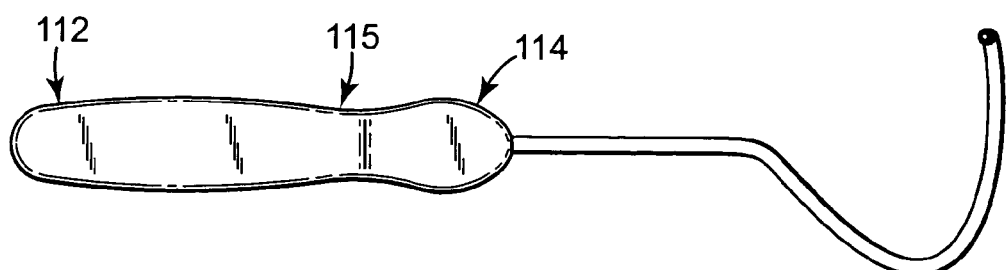
FIG. 12 is bottom view of the instrument of FIG. 8.
Figure 13:
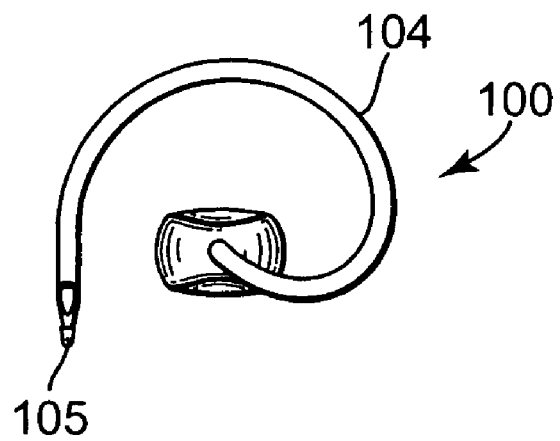
FIG. 13 is a rear view of the instrument of FIG. 8.
Figure 14:
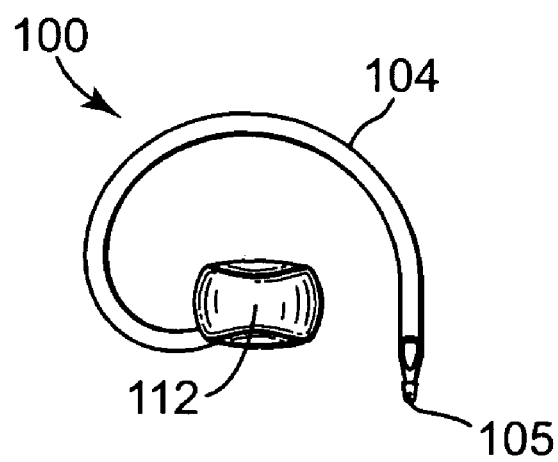
FIG. 14 is a front view of the instrument of FIG. 8.

Referring to FIGS. 1, 5 and 6, the side surfaces 34 and 36 preferably have a plurality of tactile surfaces 35 extending in a direction substantially perpendicular to the longitudinal axis A of the handle 10. Preferably, there are at least eight tactile surfaces 35 on each side 34 and 36. In a preferred embodiment, substantially all of the surfaces 35 are located on the mid and distal regions of the handle 10. The tactile surfaces may extend above the major surfaces of the handle 10, or below the major surface. They may comprise slits, slots, bumps, embossed portions, protrusions, surface treatments, ridges, ribs, grooves or the like. Optionally, the handle 10 may have such structures on any portion thereof to enhance a user's grasp.

The tactile surfaces 35 are believed to reduce the exertion required to adequately grasp the handle 10 during needle passage through tissue. The tactile surfaces increase the friction between the handle 10 and the user's hand, which stabilizes the instrument in the user's hand. This can lead to a reduction in the rotational motion of the instrument (e.g. rotational slippage) when the tip 5 is intended to move in a short, linear motion (e.g. when the tip punctures relatively tough tissue). This is also believed to provide leverage to afford convenient, efficient power transmission when it is desired to create a moment about the axis A'.

If the surgical instrument is designed for use on a particular side of a patient (e.g. the patient's right side or left side), then the handle 10 may conveniently have indicia 31. The indicia may be provided by a raised or embossed portion of the handle 10, or it may be printed on the handle. The indicia 31 is shown in this embodiment as a carrot shaped embossed portion of the handle 10. The carrot may be used to indicate on which side of the patient (relative to the patient's midline) the needle is intended to be used when the indicia is facing the user. Notably, other than the indicia 31, a handle for use with a needle for the patient's right side may be substantially identical to a handle for use with a needle designed for the patient's left side. This affords convenience in manufacturing, storing and shipping of the product.

As discussed above, a transition region is preferably present between the proximal region 12 and the distal region 14 of the handle 10. The transition region may comprise a groove or a scalloped shaped region. Conveniently, this structure may cradle the anatomical structure of a user's thumb.

The surface 29 may be ski-sloped shape and is preferably substantially symmetrical about axis A'. A surface similar to surface 29 is preferably found on the bottom 24 of the handle 10.

The materials of the handle 10 can comprise any suitable material for a surgical instrument. They are preferably polymeric materials such as, but not limited to polycarbonate, polyethylene, polypropylene, polyvinyl chloride (PVC), polytetrafluoroethylene (PTFE), delrin, ABS, polyurethane, nylon, acetal, urethane, polyetherimide, polysulfone or other similar sterilizable materials, including combinations thereof. Notably, a surgical instrument with a metal needle and a handle that has substantial polymeric portions will have less weight concentration in its handle compared with a fully metallic instrument in the same shape. It is believed that a surgical instrument with a handle that has substantial polymeric portions may have desirable handling characteristics.

The handle 10 preferably is permanently affixed to the needle of the surgical instrument. By permanently affixed, it is meant that the handle does not move relative to the needle (e.g. it is not manually repositionable or removable).

Molding, casting and machining processes may be utilized to construct the surgical instrument according to the present invention. The major surfaces of the handle 10 may comprise a monolithic, unitary or composite injection molded components.

The surgical instrument may be constructed using a molding process. First, case halves may be molded out of a suitable material (e.g. a polycarbonate). Next, the needle portions 2 and 4 may be placed in a base handle mold and the two case halves may be ultrasonically welded together around the needle portion 2. Next, a second injection molding process may be used to complete the structure of the handle 10. One or more slots on the portion of the needle portion 2 designed to be within the handle 10 can help lock the needle into the handle after the case halves have been molded (and prior to welding) by preventing rotation of the needle relative to the handle during the rotational pass of the needle tip 5 through tissue. The slots may also prevent pull out of the needle from the handle. The slots may also serve to orient the needle tip relative to the handle to ensure the desirable, proper orientation of the handle relative to the needle during construction of the surgical instrument.

A first base handle mold can form, for example, the portion of the handle 10 that does not include the tactile surfaces 35. Another base handle mold could form other structures such as the tactile surfaces 35. Polymeric materials for the handles can comprise any suitable polymer such as polycarbonate or a copolymer of acrylonitrile, butadiene and styrene (ABS). Suitable materials include RTP 300 Z Polycarbonate available from RTP Company or Bayer's Lustran ABS.

An insert or other portion of a first mold may be used to preserve room for a second injection molding (an overmold) of a second polymeric material. For example, the second injection molding may form the tactile surfaces 35 and sides 34 and 36. Any suitable polymeric material may be used for the overmolding process. Suitable examples include, but are not limited to Pellethane urethane, or Santoprene 8211-55B100 from Advanced Elastomer Systems. The second material may run through the handle 10, connecting the major surfaces.

The surgical instruments shown in FIGS. 1-7 are only embodiments of the present invention, and one of ordinary skill in the art who is exposed to this disclosure will recognize that other embodiments and representations are within the scope of the present invention. FIGS. 8-14 show another embodiment of surgical instrument 100.

The surgical instrument 100 has a needle portion with a substantially straight portion 102 and a substantially curved portion 104 terminating in a tip 105. The tip 105 is preferably blunt, but it may also be sharp or substantially sharp. An eyelet may optionally be present near the tip 105.

The needle portion is preferably constructed of a metallic material. The surgical instrument 100 also has a handle portion preferably constructed at least in part from a polymeric material. The handle portion is permanently affixed to the needle portion.

The handle portion comprises a proximal end region 112, a distal end region 114, and a transition region 115 between the proximal and distal end regions. The transition region 115 is reduced in size relative to the proximal 112 and distal 114 end regions. This reduced size of the transition region 115 affords the capacity to enhance the mechanical association between a user's hand and the handle of the instrument 100. It is believed that a user's hand can more readily conform to the shape of the handle than that of a purely cylindrical handle.

As seen in FIGS. 8-14, the proximal end region 112, distal end region 114 and transition region 115 have maximum heights and widths. Preferably, the maximum height of the transition region is less than the maximum height of the proximal end region. Also preferably, the maximum height of the transition region is less than the maximum height of the distal end region. Preferably, the maximum width of the transition region is less than the maximum width of the proximal end region. Also, the maximum width of the transition region is preferably less than the maximum width of the distal end region.

All patents, patent applications, journal articles and publications cited herein are hereby incorporated by reference in their entirety as if individually incorporated.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A handle for a surgical instrument having a needle with a substantially straight portion and a curved portion, the handle comprising:

an elongate body having a proximal end region including a proximal end, a distal end region including a distal end, top and bottom portions that define a height, and side portions that define a width;

wherein the proximal end region includes a maximum width and a maximum height, and the distal end region includes a maximum width and a maximum height;

wherein the maximum width of the proximal end region is greater than the maximum height of the proximal end region and the maximum width of the distal end region is greater than the maximum width of the proximal end region;

wherein the straight portion of the needle is adapted to project from the distal end of the body; and wherein at least the top portion has a surface that is sized and shaped to receive a user's thumb in the distal end region.

2. A handle according to claim 1 wherein the proximal end region has generally convex surfaces.

3. A handle according to claim 1 wherein the top and bottom portions have substantially flat surfaces in the distal end region.

4. A handle according to claim 1 wherein the maximum height of the proximal end region is greater than the maximum height of the distal end region.

5. A handle according to claim 1 wherein the side portions have a plurality of grasping ribs.

6. A handle according to claim 1 wherein the distal end region has fins.

7. A handle according to claim 1 wherein the handle is constructed from a polymeric material.

8. A handle according to claim 1 wherein the elongate body has an elongate axis, and the straight portion of the needle has an elongate axis, and the axis of the elongate body is parallel to the axis of the straight portion of the needle.

9. A handle according to claim 1 wherein the elongate body has an elongate axis, and the straight portion of the needle has an elongate axis, and the elongate axis of the elongate body is coaxial with the elongate axis of the straight portion of the needle.

10. A surgical instrument for treating pelvic floor disorders comprising:
  a metallic needle portion having a substantially straight portion and a substantially curved portion;
  a handle portion constructed at least in part from a polymeric material, the handle portion comprising a proximal end region, a distal end region, and a transition region between the proximal and distal end regions, each region having a width;
  wherein the transition region is reduced in width relative to the proximal and distal end regions; and
  wherein the proximal end region has a maximum height that is greater than a maximum height of the transition region and a maximum height of the distal end region.

11. A surgical instrument according to claim 10 wherein the metallic needle portion has a tip portion that is at least substantially blunt, and the curved portion is substantially helical.

12. A surgical instrument according to claim 10 wherein the metallic needle portion is constructed from stainless steel.

13. A surgical instrument according to claim 10 wherein the transition region has a maximum width that is less than a maximum width of the distal end region and a maximum width of the proximal end region.

14. A surgical instrument according to claim 10 wherein the transition region has a substantially concave surface.

15. A surgical instrument according to claim 10 wherein a length of the proximal end region is longer than a combined length of the transition region and distal end region.

16. A surgical instrument according to claim 10 wherein the distal end region comprises a pair of fins projecting from sides of the handle.

* * * * *